United States Patent
Maessen et al.

(10) Patent No.: US 12,094,594 B2
(45) Date of Patent: Sep. 17, 2024

(54) METHOD OF ESTIMATION PHYSIOLOGICAL PARAMETERS USING MEDICAL IMAGE DATA

(71) Applicant: KONINKLIJKE PHILIPS N.V., Eindhoven (NL)

(72) Inventors: Ralph Theodorus Hubertus Maessen, Roermond (NL); Sergei Shulepov, Eindhoven (NL); Marco Baragona, Delft (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 788 days.

(21) Appl. No.: 16/980,906

(22) PCT Filed: Mar. 6, 2019

(86) PCT No.: PCT/EP2019/055469
§ 371 (c)(1),
(2) Date: Sep. 15, 2020

(87) PCT Pub. No.: WO2019/174973
PCT Pub. Date: Sep. 19, 2019

(65) Prior Publication Data
US 2021/0012887 A1   Jan. 14, 2021

Related U.S. Application Data

(60) Provisional application No. 62/746,633, filed on Oct. 17, 2018, provisional application No. 62/643,218, filed on Mar. 15, 2018.

(51) Int. Cl.
*G16H 50/50* (2018.01)
*A61B 5/024* (2006.01)
(Continued)

(52) U.S. Cl.
CPC ............ *G16H 30/40* (2018.01); *G06F 30/28* (2020.01); *G06T 17/205* (2013.01); *G16H 50/20* (2018.01)

(58) Field of Classification Search
USPC ........................... 382/128–227; 600/300–587
See application file for complete search history.

(56) References Cited

U.S. PATENT DOCUMENTS

| | | | |
|---|---|---|---|
| 7,610,192 B1 | 10/2009 | Jamieson | |
| 8,935,140 B2 * | 1/2015 | Rodriguez | G06F 30/15 703/2 |

(Continued)

OTHER PUBLICATIONS

Wenbin Mao et al., Fully-coupled fluid-structure interaction simulation of the aortic and mitral valves in a realistic 3D left ventricle model ; 2017 (Year: 2017).*

(Continued)

*Primary Examiner* — Marcellus J Augustin
(74) *Attorney, Agent, or Firm* — Sherry Austin

(57) ABSTRACT

A method (12) of estimating one or more physiological parameters, in particular of a cardiac region, based on medical imaging data. An input time series of three-dimensional medical images is received (14), representative of a cardiac region of a patient. A meshless simulation framework is applied (16) for simulating blood flow through at least a portion of the anatomical area captured by the images. The simulation framework comprises in particular simulating force interactions between individual elements of a simulated fluid (representing blood) and individual patches of a tissue structure of the imaged cardiac region. One or more physiological parameters (18) are derived based on the simulated blood flow.

16 Claims, 2 Drawing Sheets

(a)

(b)

(51) Int. Cl.
*A61B 5/026* (2006.01)
*A61B 5/03* (2006.01)
*G06F 30/20* (2020.01)
*G06F 30/28* (2020.01)
*G06T 17/20* (2006.01)
*G16H 30/40* (2018.01)
*G16H 50/20* (2018.01)

(56) References Cited

U.S. PATENT DOCUMENTS

| | | | |
|---|---|---|---|
| 10,682,180 B2* | 6/2020 | Taylor | A61B 5/1118 |
| 11,331,149 B2* | 5/2022 | Mortier | G16H 30/20 |
| 11,967,435 B2* | 4/2024 | Grinstein | A61M 60/178 |
| 2007/0014452 A1* | 1/2007 | Suresh | G06T 7/0012 |
| | | | 382/128 |
| 2012/0022843 A1* | 1/2012 | Ionasec | G06T 13/20 |
| | | | 703/11 |
| 2012/0041318 A1 | 2/2012 | Taylor | |
| 2012/0215510 A1 | 8/2012 | Metaxas | |
| 2012/0259608 A1* | 10/2012 | Spilker | G06F 30/20 |
| | | | 703/11 |
| 2013/0197884 A1* | 8/2013 | Mansi | A61B 8/469 |
| | | | 703/2 |
| 2014/0071125 A1* | 3/2014 | Burlina | G06T 7/00 |
| | | | 345/420 |
| 2014/0249784 A1* | 9/2014 | Sankaran | G06T 7/0012 |
| | | | 703/2 |
| 2015/0065864 A1* | 3/2015 | Sharma | A61B 5/0263 |
| | | | 600/407 |
| 2015/0317429 A1* | 11/2015 | Peters | A61B 6/032 |
| | | | 703/11 |
| 2017/0032097 A1* | 2/2017 | Itu | G16H 50/50 |
| 2017/0109496 A1 | 4/2017 | Hisada et al. | |
| 2017/0145793 A1* | 5/2017 | Ouenes | G06F 17/18 |
| 2018/0174068 A1* | 6/2018 | Dahl | G16H 50/50 |
| 2019/0298450 A1* | 10/2019 | Dasi | G16H 50/50 |
| 2021/0280318 A1* | 9/2021 | Huo | A61B 5/026 |

OTHER PUBLICATIONS

International Search Report and Written Opinion for International Application No. PCT/EP2019/055469, filed Mar. 6, 2019, 20 pages.
Mao, et al., "Fully-coupled fluid-structure interaction simulation of the aortic and mitral valves in a realistic 3D left ventricle model", PLOS ONE, vol. 12, No. 9, Sep. 8, 2017, pp. 1-21.
Toma, et al., "High-resolution subject-specific mitral valve imaging and modeling: experimental and computational methods", Biomechanics and Modeling in Mechanobiology, vol. 15, No. 6, Apr. 19, 2016, pp. 1619-1630.
Shahriari, et al., "Evaluation of shear stress accumulation on blood components in normal and dysfunctional bileaflet mechanical heart valves using smoothed particle hydrodynamics", Journal of Biomechanics, vol. 45, No. 15, Oct. 11, 2012, pp. 2637-2644.

* cited by examiner

METHOD OF ESTIMATION PHYSIOLOGICAL PARAMETERS USING MEDICAL IMAGE DATA

RELATED APPLICATIONS

This application is the U.S. National Phase application under 35 U.S.C. § 371 of International Application No. PCT/EP2019/055469, filed on Mar. 6, 2019, which claims the benefit of both Provisional Application Ser. No. 62/643,218, filed Mar. 15, 2018 and Provisional Application Ser. No. 62/746,633, filed Oct. 17, 2018. These applications are hereby incorporated by reference herein, for all purposes.

FIELD OF THE INVENTION

This invention relates to estimating physiological parameters based on medical image data, in particular based on application of a simulation framework to medical image data.

BACKGROUND OF THE INVENTION

In the field of medical diagnostics and, in particular, cardiac diagnostics, there is a growing demand for automatic quantification of (e.g. hemodynamic) parameters from medical images. Biophysical models and simulation techniques or frameworks can provide a useful tool to assist in this. Not only can modeling and simulation help in automating and streamlining parameter measurement, in many cases, parameters not directly measurable from a medical image can be derived based on the models. Therefore, in recent years, simulation methods, known in the art of engineering, have been introduced to the medical field.

In this context, simulation methods and modeling take imaging data as an input, and, in combination with embedded knowledge regarding the behavior and physical characteristics of certain parameters of the system, derive measurements or estimates of those parameters. For instance, from medical images of the cardiac region, structural information about the heart and its valves and chambers is derivable, and from this, and the algorithms of a certain model, characteristics of blood flow through the heart structure can be simulated or modeled. From this, various parameters related to the blood flow can be derived.

A drawback of known simulation methods is that often several (manual) steps are necessary to enable simulations to be performed on the anatomical data, for example image registration, and segmentation of the images. Segmentation permits structural information about the imaged anatomical region to be extracted in a codified and organized way, so that it can be utilized by the model or simulation to simulate the parameters. Furthermore, in many cases, expertise of a specialist is required to prepare, perform, and post-process such simulations, which consumes substantial time and human resources.

Known techniques for the simulation of internal flows include for instance finite volume (FV) or finite element (FE) methods, and also Lattice-Boltzmann methods. These however are strongly dependent upon the geometrical or structural accuracy of the tissue structure information which is derived from the images and utilized by the model. There is a requirement for the imaged anatomical area to be structurally discretized in space and time, e.g. by segmentation, in order to perform the simulations of parameters pertaining to that anatomy.

This strong requirement on integrity of the structure information is problematic since even a very detailed 3D image segmentation may contain geometrical imperfections, which will fundamentally undermine the simulation accuracy. Derived parameters are therefore not reliable.

In order to remedy this, in many known techniques, a process of "repairing" segmented anatomical areas is performed, in order to satisfy the requirements for a robust simulation. This often involves skills of a professional engineer, and may take a long time depending on how severe imperfections in the segmentations are. Furthermore, in certain domains, in particular the cardiac domain, the structure of the region deforms and changes almost continually as part of the natural heart cycle. This means that re-pairing, or re-meshing, has to be performed on a very regular, repeated basis.

In addition, given the strong dependency of simulations upon the segmentation accuracy, multiple segmentation trials are often required to extract the necessary information.

A further difficulty in known simulation or modeling techniques, in particular in the case of cardiovascular applications, is the typical (relative) low frame rate (frame-per second rate) of registered image sequences, i.e. the low temporal resolution of the image sequence. Due to this lower frame-per-second (FPS) rate, synchronizing the tissue motion, e.g. left ventricle contraction upon opening and closing of the aortic and mitral valves can be difficult. The physical behavior of modeled fluids (e.g. blood) within known models and simulations is very sensitive to this imperfection.

Finally, and as mentioned above, a further problem is the frequent, severe deformation of the tissue structure in certain anatomical areas. This is particularly the case in the cardiac region, where boundaries and walls of for instance valves and ventricles deform and move almost continually. This naturally results in a repeated and relative large change in the domain topology, for instance during valve opening. In order to resolve the blood flow through the valve in an accurate manner, a domain topology re-meshing is often required. This is a non-trivial procedure and can be complex and time consuming to perform. For the re-meshing to be performed on a routine basis, as is required for the cyclic motion of the heart, a specific Lagrangian-Eulerian (ALE) solver may for instance need establishing and configuring, with automatic re-meshing triggered by certain topological changes.

This is illustrated for instance in FIG. 1, which in which schematically depicts typical volumetric meshes as may be used in finite volume (FV) simulations. In this example, aortic valve is opening, and the mesh is required to be adapted accordingly. This may even require adaptive mesh changes during the simulation to resolve the blood flow correctly.

As shown in FIG. 1, there is a relatively large change in the domain topology during aortic valve opening, leading to expansion of the surrounding anatomical region (shown as light grey shaded area) in image (a). Responsive to this, the mesh (shown as dark grey shaded region), must be expanded/re-rendered, as illustrated in image (b).

There have been proposed alternative approaches to mitigate severe deformation of meshes and avoid extensive re-meshing. These techniques are based on construction of a fictitious domain (sometimes called "level sets"). While these techniques assist in resolving some of the above mentioned problems, they will still require finer meshing in the regions of fluid jet development, and also require domains substantially larger than the original geometrical morphology.

In summary, the primary deficiencies of known ("classical") simulation technologies in the present field are as follows.

Reliable simulations are strongly dependent upon the accuracy of the tissue structure segmentation. Imperfections in the segmentation lead to breakdown in the simulation technique.

Repeated modification or repair of the anatomical segmentation is consequently required to mitigate flaws or imperfections in the segmentation.

For this reason, a skilled engineer is often required.

In view of this instability of the simulation technique, the clinical workflow may often require adapting, which is inconvenient and inefficient for the clinician.

Significant deformations in the biological tissue structure (e.g. opening of heart valves, or motion of the aorta for instance) are difficult to account for as they alter the topology of the tissue structure.

The embodiments described herein aim at providing an alternative approach to simulation-based parameter estimation capable of remedying some or all of the above identified problems.

SUMMARY OF THE INVENTION

According to examples in accordance with various embodiments, there is provided a method of estimating one or more physiological parameters based on medical imaging data, the method comprising:

receiving an input time-series of three-dimensional medical images representative of a cardiac region of a patient;

applying a meshless simulation framework to simulate blood flow through at least a portion of the imaged cardiac region, wherein the simulation framework comprises simulating force interactions between elements of a simulated fluid, representing blood, and patches of a tissue structure of the cardiac region represented by the time series of images; and determining one or more physiological parameters based on the simulated blood flow.

The terms meshless or mesh-free, as applied to simulation frameworks or techniques is a term of the art. Meshless or mesh-free methods are known from other fields (e.g. engineering) to model fluid flows, but have not previously been applied to the derivation of physiological parameters from medical image information. Meshless methods are in general those that are not based on a connection between nodes of the simulation domain (in this case the cardiac region), i.e. a mesh, but are rather based on (direct) interaction of each node with each neighboring node. As a consequence, physical extensive properties such as mass or kinetic energy are no longer assigned to elements of a general mesh but rather to individual nodes.

This avoids the problem of an inaccurate or degenerating mesh (caused by movement of tissue, as discussed above), since data points are each treated as individual physical particles with defined mass and density, rather than this physical information being embedded within a general mesh structure. In the latter case, degeneration of the mesh leads to breakdown of the physical model. Meshless frameworks are robust to this, making them better suited to scenarios in which large deformations of constraining structural features are common. Hence this makes them particularly suited for internal cardiac simulations, where deformations of the encompassing anatomical structure occurs with every heart cycle.

Hence, in meshless frameworks or techniques, no mesh is constructed. A mesh is not used for modeling blood flow or interaction of blood with the tissue structure. A mesh is neither used for extracting tissue structure information or for segmenting or identifying anatomical elements of the imaged region.

Furthermore, in the presently claimed method, forces between each of a plurality of individual fluid elements and each of a plurality of individual tissue patches are determined.

Furthermore, meshless frameworks are in general based on use of a kernel, or smoothing, function that operates on nearby data points. Interactions between particles are determined based on a sum of interactions over all particles within a given neighborhood, the range of this being defined by the smoothing length or support length of the kernel function.

Embodiments may comprise modeling force interactions directly between elements of the fluid and the bounding tissue structure, e.g. walls of vessels, ventricles and other elements of the structure of the heart or cardiac region. In other words, structural or position information pertaining to tissue of the cardiac region is used as an input for the stimulation, for instance as a constraint or set of constraints for the simulation. However, since force interactions are modeled between individual particles or elements and patches of tissue structure, changes in the domain topology do not undermine the simulations as in mesh-based techniques. Such changes are automatically dealt with by the direct force interaction modeling utilized.

Simulating the force interactions may comprise determining a force between each of a plurality of individual elements of the modeled fluid, representing blood, and each of a plurality of individual patches of the tissue structure.

The patches of the tissue structure are individual patches (portions) of the tissue. This distinguishes from other approaches, where forces are modeled in terms of an interaction of a connected mesh with fluid, where forces of the mesh system are modeled, and forces of the fluid as a whole are modeled.

The individual patches may be individually identified or separated or discretized as part of the method. This may be through a segmentation procedure applied to input time series of three-dimensional medical images.

This may be anatomical model-based segmentation.

According to some embodiments, the method may comprise generating a 4D anatomical model of the cardiac region of the patient based on the input time-series of three-dimensional medical images, the 4D anatomical model representing the tissue structure of the cardiac region, and wherein the 4D anatomical model is used as an input for the meshless simulation framework. The 4D anatomical model may be constructed based on anatomical model-based segmentation.

The 4D anatomical model may include individually identified or separated or discretized patches of the tissue structure.

A 4D (four-dimensional) anatomical model means a model representative of a three dimensional tissue structure of the cardiac region across a series of time points.

The model may be generated based on a segmentation technique, applied to the input series of three-dimensional medical images.

However, in alternative embodiments, the meshless simulation framework may be applied directly to voxels of the received series of medical images.

The simulated force interactions may comprise simulating a potential force interaction (or interaction potential) between individual elements of the simulated fluid and the individual patches of the tissue structure of the cardiac region.

The simulated force interactions may comprise a positive force component (e.g. representing an attractive force component), and a negative force component (e.g. representing a repulsive force component).

The simulated force interactions may comprise one or more components, each having an inverse power dependency upon a distance between the fluid element concerned and the tissue structure patch concerned. An inverse power dependency means that the force is proportional to a term having the aforementioned distance, raised to some power higher than one, as a denominator (or at least as a multiplier in the denominator).

Power law potentials are typical for mesoscopic interactions, and represent for instance integrated microscopic forces (e.g. Lennard-Jones potential and/or screened electrostatic molecular interactions).

By way of analogy, the potential force may be understood as a Van der Walls type force, having the form of a Van der Walls force. By this is meant that the potential effectively acts as an average or integration over microscopic forces such as Lennard-Jones potential forces. This renders the approach more efficient than determining individual microscopic forces between fluid elements and the tissue.

The potential force may be a soft mesoscopic-type interaction potential. This can be understood by analogy with for instance a Dissipative-Particle-Dynamics (DPD) type force.

The term 'soft' force is well known in the field of, in particular mesoscopic, physics and refers to a force interaction in which two objects are modeled as being able to penetrate slightly into one another at their boundaries. In other words, hard boundaries are replaced by 'soft' boundaries. As a result, forces are not governed by hard cut-off boundaries, at which values for a particle move from non-zero to zero. Instead, quantities exhibit some gradient at the boundary. This means that precise knowledge of a (tissue) boundary location is not required. Hence the model is more robust to minor inaccuracies in the tissue geometry.

The phrase soft mesoscopic refers to a type of force interaction in which individual molecular interactions, such as e.g. Lennard-Jones potentials, are not individually considered.

Instead, an integration or sum over all molecular forces is considered. As a consequence, the power dependency upon distance changes from a very high power dependency (e.g. distance to the power of 6 or 12) to a much lower power dependency (e.g. distance to the power of 1 or 2). As a result, sensitivity to minor errors in boundary position is greatly reduced, and the method is rendered more robust.

In addition, forces with lower distance power dependency are more efficient computationally, reducing processing power.

A trade-off is effectively made between accuracy of tissue boundary positions and fluid flow, in exchange for greater robustness. Unlike in known engineering applications of meshless methods, absolute precision in the position of the fluid is not essential for the purpose of determining cardiac physiological parameters, and can be compromised for improved stability of the simulation.

A DPD type force typically has an attractive part and a repulsive part. The repulsive part originates from a viscous dissipative force in the fluid. The attractive part is a deterministic, Newtonian type potential for instance.

In preferred embodiments, the meshless simulation framework is a smoothed particle hydrodynamics (SPH) simulation technique.

Smoothed particle hydrodynamics, SPH, is a well-known meshless framework in engineering fields. This approach may be understood as a meshless (or mesh-free) Lagrangian method. In this context, Lagrangian method means a method which uses the Lagrangian specification of fluid flow field, wherein fluid motion is represented using a function which follows the motion of individual moving fluid elements (or parcels) in time. The co-ordinates in this case move with the fluid. In particular, flow is represented by a function which gives the position of each fluid parcel in space at a given point in time.

This technique is advantageous as it permits the physiological parameters to be modeled in real time (due to high computational efficiency).

The meshless simulation framework may comprise applying an interaction potential (force) between elements of a simulated fluid, representing blood, and patches of the tissue structure of the cardiac region wherein the applied interaction potential force, F, has the form $$F = \frac{C_1}{R^a} - \frac{C_2}{R^b}$$

where $C_1$ and $C_2$ are pre-determined constants, R is a distance between the elements of the stimulated fluid and the patches of the 4D anatomical model of the tissue structure, and a, b are predetermined constants.

This approach is based on applying a technique known in the field of mesoscopic, colloidal physical systems but unknown in the context of meshless simulation frameworks. It is in particular based on application of a soft dissipative particle dynamics (DPD)-like interaction potential between elements representing the fluid and (moving) patches of the (e.g. segmented) cardiac structure. This can be understood by analogy with a Van der Walls (screened) type of potential force, this having the general form defined above. A Van-der-Walls type force encompasses multiple microscopic forces into a single interaction force, which is suitable in the mesoscopic field.

By 'applying' an interaction potential may be meant including an interaction potential force term within the physical equation employed by the simulation in modeling the fluid. For example, the interaction potential may be included as a term in the Navier Stokes (momentum) equation in the case that the meshless simulation framework models the fluid based on solving this equation.

The above formulation represents one example potential force which may be applied.

In further examples, any kind of screened potential which includes both a repulsive and attractive component may be used. A screened or screening potential means a potential force wherein the range of the potential extends to a certain definable cut-off distance. In other words, the potential tends to zero at some boundary distance.

The repulsion and attraction component is advantageous for compensating for missing tissue information, i.e. in the case that the tissue volume is not fully resolved.

For example, an exponential type force might also be used in further examples for simulating the interaction between fluid elements and patches of the tissue. However, an inverse power law potential is more efficient computationally, and hence may be preferred in some examples.

The defined form of interaction allows for a very stable and uniform description of the blood-tissue interaction, even where the tissue volume is not fully resolved. In particular, the fluid-structure interaction (FSI) between fluid (i.e. blood) flow and tissue elements or patches, e.g. thin-walled tissue structures (such as valves), undergoing complex deformation or motion can be handled in a very efficient way.

The use of a "soft" force field of this type in combination with an SPH simulation technique is new for the purpose of treating fluid structure interaction (FSI) in complex geometries undergoing severe deformations. It has been devised by the inventors as specifically suited for modeling fluid flow through the cardiac region. This hence allows more accurate physiological parameters to be derived, which improves patient outcomes.

The constants a and b may in examples each have a value less than 2.

The constants $C_1$, $C_2$ are force constants. Their values may be selected for the purpose of maximizing model stability.

According to one or more embodiments, the simulation framework may include modeling an aortic pressure of the imaged cardiac region based on applying (i.e. constructing or inserting or modeling) a (e.g. fictitious) fluid interface within the cardiac region and applying a repulsive potential force between the interface and elements of the modeled fluid.

In some examples, elements of the modeled fluid passing through said interface are removed from the simulation, and a cardiac output is determined based on a derived effective mass of the fluid represented by said elements passing through the interface.

Cardiac output is a well-known cardiac parameter and corresponds to the volumetric outflow of blood from the heart per unit time (e.g. liters per minute).

According to one or more embodiments, a pressure correction procedure may be applied comprising adding a pressure correction term to a pressure parameter assigned to each element of the fluid, the pressure correction term comprising a Taylor expansion of a Poisson equation for pressure.

As will be explained in greater detail below, simulating the fluid flow preferably involves solving the Navier Stokes equations for fluid flow. The Navier Stokes momentum equation includes a pressure term. The meshless simulation framework may be used to provide a modeled (discretized) expression for each of these terms, and this may be substituted into the equation. In some formulations, the meshless formulation of the terms of the Navier Stokes equation can lead to density fluctuations in the resultant simulated fluid. To compensate for this, a correction term can be added to the pressure term in the equation. In examples of the present equation, the pressure correction term may comprise a Taylor expansion of a Poisson equation for pressure.

This Taylor expansion takes the form $$\Delta p_i = -c^2 \Delta t \sum_{j=1}^{N} m_j (u_j - u_i) \cdot \nabla_i W_{ij}$$

where subscript i denotes the fluid element to which the pressure correction is applied, subscript j corresponds to each of the neighboring fluid elements or tissue structure particles, $m_j$ corresponds to mass of each element (particle) of the fluid j, u corresponds to a velocity of each element of the fluid, $W_{ij}$ corresponds to a weighting function (or smoothing function), which will be explained in further detail below, and c is the speed of sound in the fluid.

The meshless simulation framework may in this case, or in any embodiment, be a based on a weakly-compressible formulation of a smoothed particle hydrodynamics, SPH, simulation technique.

The weakly compressible formulation of SPH is already known for other applications. It is aimed at addressing the problems caused by the inherently compressible formulation used in the standard SPH approach. For complex moving boundaries full compressibility is not an accurate assumption and can lead to compression artefacts.

The weakly compressible SPH refers to an SPH formulation in which either an effective speed of sound within the modeled fluid is increased close to its realistic value, or a pressure-density relation is modeled using a stiff equation of state.

The weakly compressible SPH formulation is outlined in more detail for example in the following papers: Monaghan J. J., Smoothed particle hydrodynamics, (2005) Rep. Prog. Phys. 68:1703-1759; Monaghan J. J., (1994) Simulating free surface flows with SPH J. Comput. Phys. 110:399-406; Monaghan J. J., Gingold R. A., (1983) Shock simulation by the particle method SPH, Journal of Computational Physics 52:374-389; Becker, M. and Teschner, M. (2007). Weakly compressible SPH for free surface flows. In Proceedings of the ACM Siggraph/Eurographics Symposium on Computer Animation, p. 209-217.; Becker, M., Tessendorf, H., and Teschner, M. (2009). Direct forcing for Lagrangian rigid-fluid coupling. IEEE Transactions on Visualization and Computer Graphics, 15(3):493-503.

A weakly compressible formulation can lead to fluctuations in the density of the simulated fluid. This is because some areas may acquire greater local build-up of (fluid) particles than others, leading to non-uniform fluid density. These can be substantial in some cases, depending upon the flow conditions.

To reduce these fluctuations, a first order correction to the SPH formulation of the pressure term used in the Navier Stokes equation (outlined above) can be applied.

In this case, pressure compensation, making use for example of an expanded Poisson equation for pressure, may help to reduce fluctuations in the pressure in the simulation, and improve stability.

In particular, it is common in weakly-compressible formulations for a parameter of the meshless simulation framework representing an effective speed of sound within the simulated fluid may to be set higher than a true maximum (expected) speed of the sound itself. This speeds up simulations, since pressure (sound) propagations are effectively run at higher than true speed. To compensate for this, a pressure correction factor as defined above may be usefully applied. This factor is based on an expansion of a pressure Poisson equation (PPE) into a Taylor series.

A weakly compressible formulation is useful in particular for simulating squeezing fluid flows with thin boundary walls. This type of action characterizes much of the physical behavior of the cardiac system during heart cycles.

The weakly compressible formulation provides improved computational efficiency.

According to any examples, the pressure correction procedure may be an iterative procedure, wherein the pressure correction term is re-calculated and added to the pressure parameter at each of a series of iterations. The pressure may be corrected iteratively to avoid overcompensation. The approach multiplicatively applies a 'relaxation factor' of less than one to the full pressure correction term to effectively slow down the correction, so that it is broken down into several smaller correction steps. The correction is continued through multiple of these small steps (iterations), for instance until density fluctuations in the simulated fluid are seen to stabilize, or reach a minimum. This can be monitored simultaneously with performing the correction.

Hence the iteration for pressure correction is separate from any time-step iteration for advancing the simulation (discussed below).

In one or more embodiments, method may comprise simulating blood flow through at least the aortic and/or mitral valve of the heart.

According to any embodiment, the one or more physiological parameter measurements estimated by the method include at least one of: a pressure change from a first point in a fluid path of the cardiac region to a second point in the fluid path, a pressure change between two points along a cardiac valve, cardiac output, a flow speed of blood through a cardiac valve e.g. maximum flow speed, and a residence time for blood in a ventricle of the heart.

Residence time in a ventricle of the heart means a time spent residing, i.e. dwelling, in a ventricle of the heart.

Applying the meshless simulation framework and determining the one or more physiological parameters may be performed in real time with receipt of the three dimensional medical images.

In this case, preferably, the smoothed particle hydrodynamics (SPH) simulation technique is used.

Various embodiments described herein may be applied to input medical images of any imaging modality, including (by way of non-limiting example), ultrasound images, MRI images or CT scan images.

Examples in accordance with a further aspect of the various embodiments described herein may provide a processing unit, configured to: receive an input time-series of three-dimensional medical images representative of a cardiac region of a patient;

apply a meshless simulation framework to simulate blood flow through at least a portion of the imaged cardiac region, wherein the simulation framework comprises simulating force interactions between elements of a simulated fluid, representing blood, and patches of a tissue structure of the cardiac region represented by the time series of images; and determine one or more physiological parameters based on the simulated blood flow.

Examples in accordance with various embodiments described herein may provide a medical imaging unit comprising:

a medical imaging device for acquiring a time series of three dimensional medical images; and a processing unit as outlined above, arranged to receive the acquired time series of three dimensional images for use in said meshless simulation framework to determine the one or more physiological parameters.

The processing unit may in particular examples receive the images in real time. For example the medical imaging device may be adapted to output the images in real time with their acquisition. The processing unit may be adapted to perform the simulation framework in real time with receipt of the medical images from the medical imaging device.

The medical imaging device may include for instance any one of: an ultrasound imaging device, an X-ray imaging device, an MRI imaging device, or a CT imaging device. These represent illustrative examples only.

These and other aspects will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
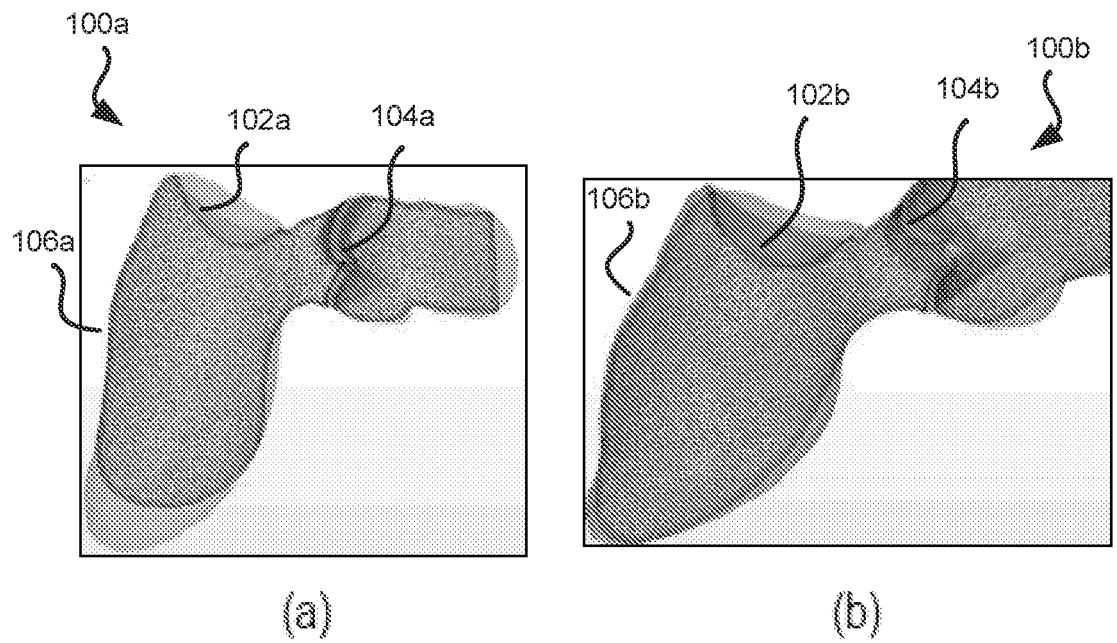
FIG. 1 illustrates a re-meshing procedure after opening of a heart valve within a known simulation framework.

The various embodiments will be described with reference to the Figures.

It should be understood that the detailed description and specific examples, while indicating exemplary embodiments of the apparatus, systems and methods, are intended for purposes of illustration only and are not intended to limit the scope of the the embodiments. These and other features, aspects, and advantages of the apparatus, systems and methods described herein will become better understood from the following description, appended claims, and accompanying drawings. It should be understood that the Figures are merely schematic and are not drawn to scale. It should also be understood that the same reference numerals are used throughout the Figures to indicate the same or similar parts.

The various embodiments may provide a method of estimating one or more physiological parameters, in particular of a cardiac region, based on medical imaging data. An input time series of three-dimensional medical images is received, representative of a cardiac region of a patient. A meshless simulation framework is applied for simulating blood flow through at least a portion of the anatomical area captured by the images. The simulation framework comprises in particular simulating force interactions between individual elements of a simulated fluid (representing blood) and individual patches of a tissue structure of the imaged cardiac region. One or more physiological parameters are derived based on the simulated blood flow.

In certain examples, the individual patches of the tissue structure may be identified or separated or discretized based on segmenting the tissue structure, i.e. the individual patches may be segmented.

Various embodiments described herein may be based on application of a meshless simulation framework. 'Meshless' or, equivalently, 'meshfree', in this context is a term of the art, and has a well-defined meaning (see for instance Liu, G. R. 2nd edn: 2009 Mesh Free Methods, CRC Press.). In particular, and as discussed above, meshless or meshfree methods are in general those that do not require connection between nodes of the simulation domain, i.e. a mesh, but are rather based on (direct) interaction of each node with each neighboring node. As a consequence, physical extensive properties such as mass or kinetic energy are no longer assigned to mesh elements but rather to the single nodes.

By contrast, in mesh-based methods, a mesh must be constructed. Each point of this mesh has a determinate number of predefined neighbors, and a connectivity between these neighbors is used to define certain mathematical operators such as the derivative. These mesh-defined operators are then used to construct equations upon which the simulation is based, for example NavierStokes equations or Euler equations.

However, in simulations in which the material structure of the modeled region can move or deform, the connectivity of the mesh becomes difficult to maintain without introducing serious error into the simulation. If the mesh for example becomes tangled or degenerate during the simulation, the operators defined on it no longer give correct values, undermining accuracy of the simulation.

As noted above a process of mesh recreation can be performed (re-meshing). However this is computationally expensive, and furthermore may also introduce further errors as all of the existing data points of the mesh must be mapped onto a new and different set of data points.

In meshless simulation frameworks or techniques, the simulation does not use a mesh, and no mesh is created. This avoids the problem of an inaccurate or degenerating mesh (caused by movement of tissue, as discussed above), since data points are each treated as individual physical particles with defined mass and density, rather than this physical information being embedded within a general mesh structure. In the latter case, degeneration of the mesh leads to breakdown of the physical model. Meshless frameworks are robust to this, making them better suited to scenarios in which large deformations of the constraining structural features (e.g. valves, arteries, ventricles, chambers) are common. Hence this makes them particularly suited for internal cardiac simulations, where deformation of the encompassing anatomical structure occurs with every heart cycle.

More particularly, in various embodiments, rather than model interactions of a mesh, forces between each of a plurality of individualized fluid elements and individualized tissue patches may be determined.

Furthermore, meshless frameworks are in general based on use of a kernel, or smoothing, function that operates on nearby data points. Interactions between particles are determined based on a sum of interactions over all particles within a given neighborhood, the range of this being defined by the smoothing length or support length of the kernel function.

According to various embodiments, the meshless simulation method used may be a smoothed particle hydrodynamic (SPH) simulation framework.

Smoothed particle hydrodynamics, SPH, is a well-known meshless technique in engineering fields. As noted above, this technique may be understood as a meshless (or mesh-free) Lagrangian method. In this context, Lagrangian method means a method which uses the Lagrangian specification of fluid flow field, wherein fluid motion is represented using a function which follows the motion of individual moving fluid elements (or parcels) in time. The co-ordinates in this case move with the fluid. In particular, flow is represented by a function which gives the position of each fluid parcel in space at a given point in time.

This framework is advantageous as it permits the physiological parameters to be modeled in real time.

SPH provides a way of discretizing the Navier Stokes equations for fluid flow in a mesh-free fashion (as will be discussed further below).

The smoothed particle hydrodynamics approach operates in general by dividing a simulated fluid into a set of discrete moving elements, i, j, known as particles.

Their Lagrangian nature permits defining of their position, $r_i$, in terms of integration of their velocity, $v_i$, i.e.

$$v_i = dr_i/dt$$

where $v_i$ is velocity, and $dr_i/dt$ is total derivative of position.

As discussed above, the method models interactions of these fluid elements via a kernel (or smoothing) function having a characteristic radius, known as the "smoothing length", h. The physical quantity of any fluid element (particle) can accordingly be obtained by summing the relevant properties of all the particles that lie within the range, h, of the kernel, this being used as a weighting function W. The kernel function effectively spreads the properties of each particle in the simulated fluid over a continuum. Because of this, SPH is often called "an interpolation method for particle systems".

Since SPH is effectively an interpolation method for a particle system, it is based on evaluation of a (physical) quantity in any point in space, based on a continuum of particles, and not based only on a single discrete particle.

In order to evaluate a quantity A at a point r, the following approximation to the more general integral:
is used:

$$A_S(r) = \sum_j A_j V_j W(r - r_j, h)$$

where the interpolation integral has been exchanged for a weighted summation of all the particles j around the point r. $A_j$ is the value of A at the position of particle j, $V_j = m_j/\rho_j$ is the effective particle volume, $m_j$ is the mass of the particle, $\rho_j$ is the density of the particle, and $W(|r-r_j|,h)$ is the weighting factor, and h is the maximum distance over which the summation is performed. The function W is also called the smoothing kernel, because it smooths the particle values throughout continuous space. The distance h can be understood as a characteristic radius of the smoothing function W, and is otherwise known as the smoothing length.

In general, the smoothing function W preferably possesses a number of particular properties. First, the function should decrease with increasing distance from the point under consideration. The points closer to r will have more significant contribution to the properties of the fluid at this point than those farther away. Second, the kernel should tend to zero at distances equal to or greater than h. Third, the kernel should be symmetric about two interacting particles. Finally, the smoothing kernel should be normalized over the distance h. The normalized smoothing kernel preferably satisfies the following equations $$\int_\Omega W(r,h)dr = 1$$

$$W(r,h) \geq 0$$

$$W(r,h) = W(-r,h)$$

Solving of the Navier Stokes equations (discussed below) requires calculating the first and second derivatives of various quantities. In the SPH formulation, these may be derived from the equations above. A symmetrized gradient form of such derivatives may be expressed as:

$$\nabla A_S(r) = \rho \sum_j \left( \frac{A_j}{\rho_j^2} + \frac{A}{\rho^2} \right) m_j \nabla W(r - r_j, h)$$

The equation for the SPH value of a scalar quantity includes both a mass and a density term. This is because each particle represents a small volume:

$$V = \frac{m}{\rho}$$

The Navier-Stokes equations for an incompressible fluid (such as water) typically assume that the density term $\rho$ is constant. However, due to the nature of SPH, maintaining a constant density is very difficult.

Since in applications for determining cardiac parameters, accuracy is less important than realism and speed, for the purposes of one or more embodiments, the requirement for constant density is ignored.

To compensate for this, a density restoring force (pressure) can in a later stage of the calculation be rendered very strong.

To calculate (non-constant) density at a given position, the SPH equation above can be applied to yield:

$$\rho(r_i) = \sum_j \rho_j \frac{m_j}{\rho_j} W(r_i - r_j, h) = \sum_i m_j W(r_i - r_j, h)$$

Further details on the standard formulation of the Smoothed Particle Hydrodynamics simulation technique will be known to the skilled person, and may be found for instance in the following references: Monaghan J. J., Smoothed particle hydrodynamics, (2005) Rep. Prog. Phys. 68:1703-1759; Kelager M., (2006), Lagrangian Fluid Dynamics Using Smoothed Particle Hydrodynamics, Department of Computer Science, University of Copenhagen, Report.; Crespo A. J. C., (2008), Application of the Smoothed Particle Hydrodynamics model SPHysics to free-surface hydrodynamics, PhD theses.

Specific examples detailed below may refer in particular to use of a smoothed particle hydrodynamics technique. However, this is by way of illustration only, and it is to be understood that other meshfree methods may alternatively be used, as will be known to the skilled person.

Example methods according to embodiments may be realized as a post-processing step on 4D medical data. By 4D medical data is meant 3D + time, i.e. a time series of three-dimensional medical images.

Example methods according to the various embodiments described herein may allow for estimation or determination of a variety of clinically relevant parameters, including by way of example:

a pressure drop over cardiac valves (e.g. aortic valve);
ejected volume fraction/cardiac output;
a maximum flow speed in the fluid jet through a valve (and in particular, the aortic valve, which can be linked for instance to aortic valve stenosis);
residence or dwell time maps for blood in the left ventricle (LV); and
derivatives of the above, including e.g. a pressure-volume loop and flow structures.

The above parameters are not always derivable using standard minimally invasive measurement techniques (e.g. 4D CT data sequences). Various embodiments described herein may permit additional parameters to be derived by virtue of use of a blood flow simulation.

Figure 2:
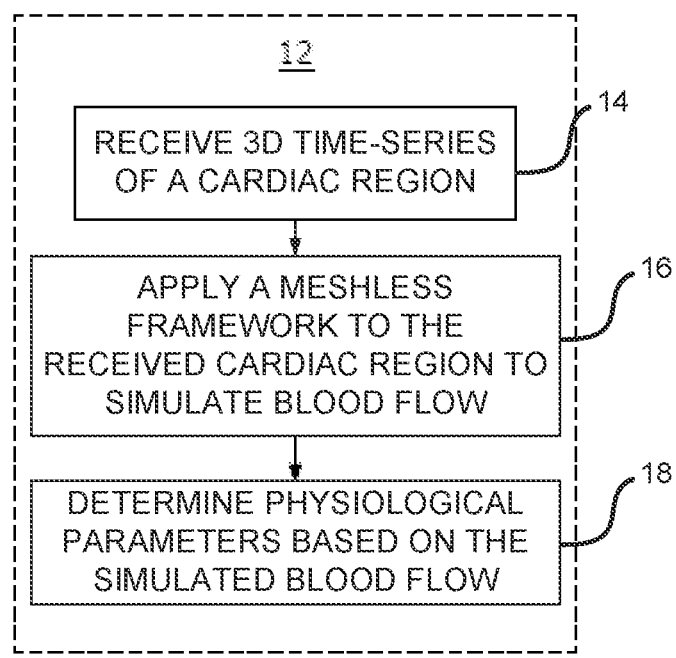
FIG. 2 shows a block diagram of an example method according to one or more embodiments.

An example method of estimating one or more physiological parameters based on medical imaging data according to various embodiments is shown in block diagram form in FIG. 2.

The example method 12 comprises:
receiving 14 an input time-series of three-dimensional medical images representative of a cardiac region of a patient;
applying 16 a meshless simulation framework to simulate blood flow through at least a portion of the imaged cardiac region, wherein the simulation framework comprises simulating force interactions between elements of a simulated fluid, representing blood, and patches of a tissue structure of the cardiac region represented by the time series of images; and
determining 18 one or more physiological parameters based on the simulated blood flow.

As discussed above, the use of a meshless simulation framework obviates the numerous problems associated with degradation or degeneration of a constructed mesh.

Furthermore, the example method is based on simulating force interactions directly between individual elements of the simulated fluid (blood) and, e.g. segmented, patches of the tissue structure.

To extract structural information, concerning e.g. the structure, position and topology, of the cardiac tissue from the imaging data, segmentation may be applied. The tissue structure patches may be individually identified or separated or discretized based on segmentation for instance.

The segmentation is preferably anatomical model-based segmentation. This type of simulation applies specific anatomical information or knowledge to the image segmentation to identify segmented components or patches anatomically, i.e. locate them anatomically.

Additionally or alternatively, structural information may be extracted from the imaging data based on construction from the imaging data of a 4D (four-dimensional) anatomical model of the cardiac region. This 4D anatomical model represents the tissue structure of the cardiac region. The 4D anatomical model may then be used as an input for the meshless simulation framework.

Construction of the 4D anatomical model may be based on use of anatomical model-based segmentation.

The 4D model of the tissue structure may in particular provide as an input for the simulation technique relevant position information over time for the imaged region permitting the force interactions with the tissue patches, referred to above, to be derived.

The model is not a mesh, and not used as a mesh for simulating the fluid flows. It defines no web of connected points or nodes. Rather the model simply embodies structural/geometrical information relating to the cardiac region, this structural information being used as an input to the mesh-free simulation technique—i.e. to inform the direct force interactions between the fluid elements and the cardiac tissue structure boundaries.

Alternatively still, the simulation technique may be applied directly to the input time series of three dimensional medical images, i.e. to the voxels of said images. The absence of a need for a mesh makes this possible.

As noted above, simulating the blood flow in the cardiac region aims at solving Navier-Stokes equations for the cardiac region, these being constrained by the patient-specific 4D anatomical motion during a heart cycle. This is further constrained according to the available time resolution (i.e. the frame or step rate) of the received series of 3D medical images.

The SPH simulation method provides for instance a way of discretizing the Navier Stokes equations in a mesh-free fashion, allowing them to be solved for the particular fluid system in question.

The Navier-Stokes equations are partial differential equations describing the momentum and mass conservation for fluid flow, depending on the velocity u and pressure p of the fluid, as well as the fluid density ρ and dynamic viscosity μ. A general form of the Navier-Stokes momentum equation for incompressible fluid flow over time t can be expressed as follows:

$$\rho\left(\frac{\partial u}{\partial t} + u \cdot \nabla u\right) = -\nabla p + \mu \nabla^2 u + f$$

where, in addition to the quantities outlined above, t is time, and $f$ represents external forces acting on the system, e.g. gravity, initial accelerations, electrostatic accelerations.

For the incompressible formulation, to this may also be added the further equation $\nabla \cdot u = 0$.

Since the simulated fluid represents blood, the density and dynamic viscosity may be set at generic values across healthy individuals for blood density and dynamic viscosity.

Solving this equation for the various fluid pathways (e.g. including heart valves and/or ventricles and/or arteries derives a fluid velocity field u (r) where r is position within the cardiac system being modeled.

Embodiments may provide a solution to these equations, to derive a flow velocity based on application of a meshless simulation technique to simulate the blood flow through the cardiac region.

More particularly, as noted above, SPH allows evaluation of a quantity, i.e. a physical property, for particles in a fluid at a particular point in space based on integration over a field or volume of particles around that point in space. The outcome of this integration gives the physical quantity at that point in space at a particular time.

The SPH equations can be applied to derive the various quantities in the Navier Stokes equation, in order to solve Navier Stokes for a given scenario. Solving the Navier Stokes equation yields an acceleration quantity for each particle in the fluid, and new particle position can be derived by integrating this expression numerically over time.

In particular, since for a fluid, the acceleration-density is the full time derivative of the velocity field $$\frac{d}{dt}u(t, r(t)) = \left(\frac{\partial}{\partial t} + u \cdot \nabla\right)u$$

therefore acceleration of each particle can be expressed as:

$$a_i = \frac{du_i}{dt} = \frac{F_i}{\rho_i}$$

where $a_i$ is acceleration, $du_i/dt$ is the total derivative of velocity, and $F_i$ is the sum of all the force terms on the right hand side of the Navier Stokes equation above. In order to simulate the particle motion in the frame of SPH, it is necessary to express each of the force terms through its discrete representation (i.e. the representation derived using the meshless simulation framework, for example SPH).

Once each term has been expressed in an appropriate SPH formulation, numerical time integration is performed. In particular, in order to simulate the fluid flow, each particle is advanced through time using a global, fixed time step Δt. At every time point, the above acceleration equation is employed, with each component expressed in SPH formulation, to compute particle acceleration. The new particle position for a particle at a given time is then derived by integrating this acceleration numerically over time.

The integration over time can be performed in some examples using an implicit integration scheme. For example, an implicit Euler scheme may be applied. The implicit Euler scheme may in fact be understood as a semi-implicit method because only particle position is updated in an implicit fashion. The semi-implicit Euler scheme is based on the explicit Euler formulation, which is a well-known integration method. In the explicit Euler scheme, position and velocity are updated in parallel as $$dr = u \cdot dt$$

$$du = a \cdot dt$$

The above equations may be discretized, for example, using semi-implicit Euler schema. In a semi-implicit Euler scheme, the position increment depends upon the result from the velocity increment, meaning that position and velocity are no longer independent:

$$u_{t+\Delta t} = u_t + \Delta t a_t$$

$$r_{t+\Delta t} = r_t + \Delta t u_{t+\Delta t}$$

In this way, corrections made to the acceleration term $a_t$, as part of the meshless simulation framework are automatically transferred to both the velocity and position update.

The meshless simulation framework according to various embodiments may involve simulating force interactions between individual elements (or particles) of the simulated fluid (blood) and individual patches of the tissue structure of the cardiac region. These force interaction may then be used as one component of the aggregate force term $F_i$ in the Navier Stokes acceleration equation above.

As noted above, individual patches of the tissue structure may be identified or individualized, for instance based on a segmentation procedure applied to the input time-series of medical images. The patches are the primitives defining the tissue surface, for instance after segmentation. These may for instance be patches of the segmented meshes, or bi-splines in a parametrical description.

In a preferred set of embodiments, the simulated force interactions comprise simulated potential (force) interactions between the individual elements of the simulated fluid and the individual patches of the tissue structure of the cardiac region. This involves determining for each particle a force term representative of this force interaction, where this force term is then included within the aggregate force term $F_i$ in the Navier Stokes acceleration equation outlined above.

The simulated force interactions may comprise power law forces for example. Power law forces are forces governed a force equation having one or more components, each component having an inverse power dependency upon a distance between the fluid element concerned and the tissue structure patch concerned.

Power law forces represent a certain characteristic kind of force, and have not previously been applied in SPH simulation methods in particular. This is because such forces are applicable specifically in the case of Cardiac fluid systems, have not previously been considered in the context of meshless simulation methods.

As discussed, certain embodiments make use of the well-established meshless technique of Smoothed Particle Hydrodynamics (SPH).

For various embodiments, a number of particular adaptations may have been developed to this technique, to adapt it specifically for use in modeling cardiac flows.

These adaptations will now be discussed in detail.

According to a first adaptation of the SPH simulation framework, an interaction between elements of a modeled fluid (representing blood) and patches of the tissue structure (e.g. the 4D anatomical model) is modeled by a soft-mesoscopic interaction potential applied between these elements.

The term 'soft' force is well known in the present technical field and refers to a force interaction in which two objects are modeled as being able to penetrate slightly into one another. In other words, hard boundaries are replaced by 'soft' boundaries. As a result, forces are not governed by hard cut-off boundaries, at which values for a particle move from non-zero to zero. Instead, quantities exhibit some gradient at the boundary. This means that precise knowledge of a (tissue) boundary location is not required. Hence the model is more robust to minor inaccuracies in the tissue geometry.

The phrase soft mesoscopic refers to a type of force interaction in which individual molecular interactions, such as e.g. Lennard-Jones potentials, are not individually considered.

Instead, an integration or sum over all molecular forces is considered. As a consequence, the distance power dependency moves from a very high power (e.g. distance to the power of 6 or 12, to a much lower power dependency, e.g. distance to the power of 1 or 2. As a result, sensitivity to minor errors in boundary position is greatly reduced, and the method is rendered more robust.

In addition, forces with lower distance power dependency are more efficient computationally, reducing processing power.

A trade-off is effectively made between accuracy of tissue boundary positions, and fluid flow, in exchange for greater robustness. Unlike in known engineering applications, absolute precision in position for fluid is not essential for the purpose of determining cardiac physiological parameters, and can be compromised for improved stability of the simulation.

The applied interaction potential may also be understood by analogy to Dissipative-Particle-Dynamics (DPD) type forces. A DPD type force typically has an attractive part and a repulsive part. The repulsive part originates from a viscous dissipative force in the fluid. The attractive part is a deterministic, Newtonian type potential.

Hence a soft mesoscopic interaction potential between Lagrangian elements representing the fluid, and moving interface patches of the segmented tissue structure is introduced. For reasons described above, this type of interaction allows for stable and uniform description of the blood-tissue interaction even when the tissue structure is not fully resolved.

In particular, a fluid structure interaction (FSI) between blood flow and tissue elements undergoing very complex deformation or motion, e.g. thin-walled tissue structures (e.g. valves), can be successfully handled in a very efficient way.

In more detail, this adaptation is based on applying a concept known in the field of mesoscopic, colloidal physical systems which has not however previously been applied in SPH simulation frameworks. This approach is based on representing biophysical interactions between larger objects by a Van der Walls (screened) type of potential (force).

According to an advantageous set of examples, the potential may have the following general form:

$$F = \frac{C_1}{R^a} - \frac{C_2}{R^b}$$

where $C_1$ and $C_2$ are force constants, R is a distance between the element of the stimulated fluid concerned and the patch of the 4D anatomical model of the tissue structure concerned, and a, b are predetermined constants.

As noted, by way of analogy, the potential force may be understood as a Van der Walls type force, having the form of a Van der Walls force. By this is meant that the potential effectively represents or acts as an average or integration over microscopic forces such as Lennard-Jones potential forces. This significantly reduces the power dependency of the force. For example, the force can be changed from one having dependency upon distance raised to a power of 6-12, to one with dependency upon distance raised only to a power of 1 or 2.

The constants a and b are typically given a value less than 2 (a, b<2). The values of $C_1$, $C_2$, i.e. the force constants, may be chosen so as to maximize the stability of the model. Maximizing stability may mean for example minimizing density fluctuations in the simulated fluid. The values of a and b can be optimized for this by iteratively altering them and monitoring resultant fluctuations in pressure in the simulations.

By way of example, a value of 2 for both a and b has been found to maximize stability in the case of (e.g. planar-type) surfaces. A value of 1 has for example been found to maximize stability in the case of spherical-like surfaces.

Power law potentials are typical for mesoscopic interaction, and represent integrated microscopic forces (e.g. Lennard-Jones potential and/or screened electrostatic molecular interactions).

The above force field is applied between the fluid comprising Lagrangian particles (or fluid elements) and the segmented anatomical tissue patches. More particularly, the force term may be computed for each particle in a discretized fashion using for instance the SPH integral formula outlined above, and then this term is incorporated into the aggregate force term $F_i$ in the Navier Stokes acceleration equation outlined above, to derive acceleration for the particle.

As noted, R is the distance (range) between the relevant Lagrangian fluid element and the relevant tissue structure patch. The full range of the interaction is confined to a single support (or smoothing) length of the SPH kernel (see above).

The defined force field includes a repulsive (i.e. negative) component and an attractive (positive) component. The repulsive component effectively prevents the modeled fluid element from penetrating the tissue, and also compensates for particle depletion in the tissue in the general SPH framework.

Particle depletion is a common problem within the SPH framework, particularly in the case of moving boundaries. The moving boundaries can push particles outside of the boundaries. By including a repulsive component in the modeled force, as proposed above, this keeps particles close to, but separated from, the tissue surface and avoids penetration through the surface. Hence particle depletion is reduced.

The attractive part of the interaction ensures fluid elements present in the boundary layer (i.e. the layer of fluid directly adjacent the tissue-fluid boundary) stay close to the tissue interface.

Two specific examples will now be outlined of typical force fields which have been found by the inventors to result in a stable SPH formulation.

In a first example, the force-field may be modeled as a classical repulsive/attractive force field. In a most simple (low power law) example, this may take the following form:

$$F = C_F \left[ \frac{1}{r + (\text{Range} \cdot h)} - \frac{1}{(\text{Range} \cdot h)} \right], \text{ when } r < h$$

where $C_F$ is a force constant, r is the normal (i.e. perpendicular) distance between Lagrangian elements of the fluid and the tissue structure interface, range defines interaction range of the force, and h is the support length of the SPH kernel. The range is confined to values between 0 and 1, and typically takes a value between 0.1-0.5. The force constant CF defines the strength of the interaction, and typically depends upon the SPH formulation used.

In a second example, the force field may be modeled as a potential well type force field. This may take the general form:

$$F = C_F \left[ \frac{1}{(\text{Range} \cdot h)} - \frac{1}{r} \right], \text{ when } r < h$$

This type of interaction positions a particle layer interface (an interface between the simulated fluid and a tissue boundary, e.g. between the simulated blood and an artery wall for instance).

Fluid elements within this modeled layer follow closely the motion and deformation of the fluid-tissue interface. Fluid elements in the bulk fluid are modeled as coupled to the boundary layer elements via the SPH integral, which as discussed above spreads the properties of individual particles over a continuum extending to a characteristic radius around the particle.

A pressure distribution close to the tissue interface is compensated by an appropriate choice of the force constant $C_F$ and interaction range, range. Typical values for the range constant may for instance be between 0.25-0.5 for delivery of sustainable results. The force constant $C_F$ again depends on the particular SPH formulation used in the model.

The first and second examples of potential force fields outlined above represent principally different concepts in realizing fluid-tissue interaction. While the first example represents a classical mesoscopic interaction potential (used in micro- and mesoscopic interaction simulation frameworks), the second example is a specialized potential based on a combination of (corrected) interfacial fluid elements with the SPH formulation.

Either of the above formulations may be used in any scenario. The second approach has been found to generally lead to a more stable simulation however.

As noted above, the values of a, b, are typically constrained below 2. However, higher values can also be used. This hence corresponds to a higher order potential. For higher order potentials, additional measures may also be implemented for further stabilizing simulations, which will not be outlined in detail in this disclosure.

A second adaptation of the SPH simulation framework provided in examples may involve applying an outflow boundary condition aimed at representing or modeling an aortic pressure in the cardiac region.

More particularly, in this adaptation, the simulation technique includes modeling an aortic pressure of the imaged cardiac region based on applying a semi-transparent fluid interface within the cardiac region and applying a repulsive potential force between the interface and elements of the modeled fluid. Elements of the modeled fluid passing through said interface are removed from the simulation, and a cardiac output is determined based on a derived effective mass of the fluid represented by said elements passing through the interface. This may also allow for geometrical model reduction and numerical stabilization of the model.

The interface is implemented at the boundary between the tissue and the fluid. This obviates problems when applying known meshless simulation methods to the cardiac domain wherein particles tend to experience a pushing force toward the boundary. The repulsive potential force corrects for this.

A third adaptation of the SPH simulation framework provided in examples of of various embodiments may involve application of a pressure correction procedure comprising adding a pressure correction term to a pressure parameter assigned to each element of the modeled fluid, the pressure correction term comprising a Taylor expansion of a Poisson equation for pressure.

The pressure parameters may refer in particular examples to the SPH formulation of the pressure term in the Navier Stokes equation outlined above. In particular, applying the SPH formulation directly to the quantity of pressure, symmetrizing with respect to i and j, to comply with the reciprocity condition, and re-arranging for purposes of speed and stability yields the expression:

$$f_i^{pressure} = -\sum_{j \neq i} \frac{p_i + p_j}{2} \frac{m_j}{\rho_j} \nabla W(r_i - r_j, h)$$

This pressure term may then be substituted into the Navier stokes equation for deriving particle acceleration and, by numerical integration, particle position.

To explain further, the fundamental state variables of any individual particle are: mass, density, and velocity. Thus, pressure may be calculated in terms of these parameters. In case of an ideal gas, pressure is related to density through the equation of state, $pV=k(=nRT)$, where k is the gas "stiffness", $k=c_s^2$, with $c_s$=speed of sound in the fluid.

This equation of state results in purely repulsive forces between particles. This is true for an ideal gas that tends to expand in space. By contrast, liquids tend to exhibit internal cohesion and have a constant mass-density at rest.

A modified version of the ideal gas state equation, with an additional rest pressure $p_0$, may instead be used, which results in $$p=k(\rho-\rho_0)$$

where $\rho_0$ is the rest density. By performing this substitution, the value of p is reduced. As a consequence, the overall error in the computation is also reduced.

Frequently, an effective stiffness is chosen, which does not correspond exactly to the real speed of sound in the fluid. The choice of the effective stiffness is based on a balance between accuracy and speed of the computations. As a result, the simulation will be numerically more stable.

The above represents one standard approach which is taken in SPH for engineering applications, where accuracy is of critical importance. It is applied typically in cases in which a fully compressible SPH formulation is used.

Returning to the method, the above mentioned pressure correction approach may in examples be advantageously applied in the case that a weakly compressible constitutive formulation of the simulation framework is applied.

Hence in this case, or in any embodiment, a weakly compressible formulation of a smoothed particle hydrodynamics, SPH, simulation framework may be used.

A weakly compressible formulation is useful in particular for simulating squeezing fluid flows with thin boundary walls. As discussed above, this type of action characterizes much of the physical behavior of the cardiac system during heart cycles.

The weakly compressible formulation of SPH is already known for other applications. It is aimed at addressing the problems caused by the inherently compressible formulation used in the standard SPH approach. For complex moving boundaries full compressibility is not an accurate assumption and can lead to compression artefacts.

The weakly compressible SPH refers to an SPH formulation in which either an effective speed of sound within the modeled fluid is increased close to its realistic value, or a pressure-density relation is modeled using a stiff equation of state.

In particular, for a weakly compressible formulation, the following equation of state (Tait's Equation) may for example be used:

$$p = B\left(\left(\frac{\rho}{\rho_0}\right)^\gamma - 1\right)$$

$$B = \frac{\rho_0 c_s^2}{\gamma}$$

where p is pressure, $p_0$ is the additional rest pressure term mentioned above, and c is the speed of sound in the fluid. The value of $\gamma$ may typically be taken as $\gamma=7$. In cases where fluid density fluctuations are small, i.e. $(\rho-\rho_0)/\rho_0 \ll 1$, Tait's formulation above may be converted into the linear equation of state outlined above.

The weakly compressible formulation significantly improves robustness of the simulation, by sacrificing some degree of accuracy in fluid and boundary positions. For the purposes of determining physiological parameters however, accuracy is not as critical as in engineering applications.

The weakly compressible SPH formulation is outlined in more detail for example in the following papers: Monaghan J. J., Smoothed particle hydrodynamics, (2005) Rep. Prog. Phys. 68:1703-1759; Monaghan J. J., (1994) Simulating free surface flows with SPH J. Comput. Phys. 110:399-406; Monaghan J. J., Gingold R. A., (1983) Shock simulation by the particle method SPH, Journal of Computational Physics 52:374-389; Becker, M. and Teschner, M. (2007). Weakly compressible SPH for free surface flows. In Proceedings of the ACM Siggraph/Eurographics Symposium on Computer Animation, p. 209-217.; Becker, M., Tessendorf, H., and Teschner, M. (2009). Direct forcing for Lagrangian rigid-fluid coupling. IEEE Transactions on Visualization and Computer Graphics, 15(3):493-503.

A weakly compressible formulation can lead to fluctuations in the density of the simulated fluid. This is because some areas may acquire greater local build-up of particles than others, leading to non-uniform fluid density. These can be substantial in some cases, depending upon the flow conditions.

To reduce these fluctuations, a first order correction to the SPH formulation of the pressure term used in the Navier Stokes equation (outlined above) can be applied.

In preferred examples, this pressure correction term is based on an expansion of the pressure Poisson equation (PPE) into a Taylor series as follows:

$$\Delta p_i = -c^2 \Delta t \sum_{j=1}^{N} m_j (u_j - u_i) \cdot \nabla_i W_{ij}$$

where subscript i denotes the fluid element to which the pressure correction is applied, and subscript j corresponds to each of the neighboring fluid elements or tissue structure particles This term may then be added to the pressure term in the SPH formulation of the Navier Stokes equation outlined above.

Here, rather than solving the Poisson pressure equation directly, it is developed in the Taylor Series, based on an assumption that the pressure fluctuations are small.

Taking just the first term in the Taylor series, an iterative procedure may advantageously be employed to compensate for the compressibility.

The inventors have found that 1 to 2 iteration steps will reduce density fluctuations significantly. The first order correction takes the form set out above ($\Delta p_i$).

The pressure correction scheme is preferably applied iteratively. The (corrected) pressure term at each new iteration may be expressed as $$p_i^{i+1} = p_i + \gamma \cdot \Delta p_i$$

where $\gamma$ is the relaxation factor, set at a value lower than 1. In tested simulations, a relaxation factor was applied in the range of 0.1-0.25.

The pressure may be corrected iteratively to avoid overcompensation. The approach uses a 'relaxation factor' of less than one to effectively slow down the correction, so that it is broken down into several smaller correction steps. The correction is continued through multiple of these small steps (iterations) until density fluctuations are seen to stabilize, or reach a minimum. This can be monitored simultaneously with performing the correction.

Hence the iteration for pressure correction is separate from any time-step iteration for advancing the simulation discussed above.

As noted above, this correction may be applied in a weakly compressible formulation in which the effective speed of sound in the fluid is increased. In general, the higher the speed of sound, the fewer iterations that are required.

Expansion of a pressure Poisson equation (PPE) into a Taylor series is known in the literature. See for example Bao B. K., Zhang H., Zheng L., and Wu E., (2009) Pressure corrected SPH for fluid animation, Comp. Anim. Virtual Worlds, 20: 311-320.

In one example for instance, an effective speed of sound may be selected in the range of 10-50 times the maximum speed of the modeled fluid. In this case, a single term correction is sufficient, which is simply introduced once in the SPH formulation of the pressure term in the Navier Stokes acceleration equation Where the implicit formulation for time integration (discussed above) is used, this correction is then automatically applied both to the calculated fluid particle velocity at each time step (on inner iteration), and the fluid particle position at each time step.

In some examples, standard Sheppard regularization may be further performed at certain time-step intervals, for instance at every 50th time step.

The three above described adaptations to the standard SPH simulation framework specifically adapt the SPH framework for modeling fluid flows in the cardiac region, which is characterized in particular by frequent and large deformations and motion in the tissue structure.

Various embodiments described herein may permit simulation of blood flow through the heart or cardiac region 106a, 106b of, for example, a generated 4D anatomical model 100a, 100b. In particular examples, the method may comprise simulating blood flow through at least the aortic 104a, 104b and/or mitral valve 102a, 102b of the heart.

Based on the simulated blood flow, one or more physiological parameters may be derived. These may include one or more of: a pressure change from a first point in a fluid path of the cardiac region to a second point in the fluid path, a pressure change between two points along a cardiac valve, cardiac output, a flow speed of blood through a cardiac valve, and a residence time for blood in a ventricle of the heart.

In some examples, a maximum blood velocity in an aortic jet can be derived. This is linked to the degree of aortic valve stenosis.

The derived blood flow simulations have improved accuracy and robustness compared to known approaches, for the explained reason that the simulation frameworks applied are not dependent on geometrical integrity of a mesh.

According to certain applications, the derived blood flow simulation may be used to assist or supplement certain minimally invasive measurement techniques. For example, blood flow through the valves can be rendered or visualized in an efficient and clear manner, which may facilitate interpretation of 2-D or 3-D color Doppler ultrasound images derived from ultrasound data for example. For example, simulation results may easily be superimposed upon medical images to facilitate interpretation of flows through those images.

More generally, visualization of the blood flow simulation results may be utilized as a reference for performing or interpreting any kind of parameter measurement technique including for instance non-invasive measurements such as B-mode or color Doppler ultrasound.

To illustrate the various embodiments more clearly, a specific example of the method for estimating physiological parameters using a meshless simulation framework will now be described in detail. This represents a summary of what has already been described above. This method represents only one example, presented for illustration, and features of it should not be construed as limiting.

According to this example, in a first step, a time-series of three-dimensional medical images is received. By way of example, these may be ultrasound or MRI or CT images for instance. These may be received directly from a medical device configured for acquiring the images, for instance in real time, or alternatively may be received for instance from a memory or other data store in which they have been pre-stored.

These images are subsequently segmented to identify anatomical landmarks. This may be based on anatomical model-based segmentation.

Subsequently, an SPH formulation for each of the terms in the Navier-Stokes acceleration equation (outlined above):

$$a_i = \frac{du_i}{dt} = \frac{F_i}{\rho_i}$$

is formulated and substituted into the acceleration equation. Here $u_i$ is velocity of fluid particle i (where $u_i = dr_i/dt$), and $\rho_i$ is pressure. $F_i$ is equal to the sum of all terms on the right hand side of the Navier Stokes momentum equation, i.e.

$$F_i = -\nabla p + \mu \nabla^2 u + f$$

where, in addition to the quantities outlined above, t is time, p is pressure, and $f$ represents external forces acting on the system, e.g. gravity, initial accelerations, electrostatic accelerations.

Included in $f$ may be terms for gravity and surface tensions.

Also included in $f$ is an interaction potential of the general form $$F = \frac{C_1}{R^a} - \frac{C_2}{R^b}$$

This was discussed in detail above, including specific examples for the force which may be used. This force term represents an interaction potential between fluid elements and patches of the tissue structure.

For the pressure term p, the following SPH formulation of the pressure may be used $$f_i^{pressure} = -\sum_{j \neq i} \frac{p_i + p_j}{2} \frac{m_j}{\rho_j} \nabla W(r_i - r_j, h)$$

where $p_i$, $p_j$, is pressure at particle i, j, $m_j$ is mass of particle j, $\rho_j$ is fluid density at particle j, W is the smoothing function, and h is the smoothing length. These terms are explained in detail above.

To this pressure term is added a pressure correction term $\Delta P$ (discussed above), which takes the form of a first order Taylor expansion of the Poisson pressure equation. This is first calculated in an iterative manner, via $$p_i^{i+1} = p_i + \gamma \cdot \Delta p_i$$

where $$\Delta p_i = -c^2 \Delta t \sum_{j=1}^{N} m_j (u_j - u_i) \cdot \nabla_i W_{ij}$$

The iteration continues until density fluctuations in the fluid are reduced below some threshold. The resultant pressure correction terms is then added to the main SPH pressure term noted above, and this is introduced as a term of $f$ in the Navier-Stokes acceleration equation above.

Once all terms are introduced into the Navier stokes acceleration equation. This is then integrated numerically with respect to time, in order to derive an updated velocity and position of the particle i. The calculation is done for all particles modeled in the fluid. The integration is repeated at each new time interval in order to advance the fluid system through time, and model the flow of the fluid.

Preferably, the semi-implicit Euler scheme is used for the integration, which takes the form $$u_{t+\Delta t} = u_t + \Delta t a_t$$

$$r_{t+\Delta t} = r_t + \Delta t u_{t+\Delta t}$$

where $a_t$ is the Navier Stokes acceleration. The semi-implicit Euler scheme is discussed in detail above.

The above represents just one example workflow of the method, and should not be considered limiting of the embodiments described herein.

The simulations frameworks or techniques discussed in the present disclosure may be realised as a post-processing step on segmented and/or registered time-sequences of three-dimensional images. The simulation technique may in particular examples be run using a combination of a central processing unit (CPU), and graphics processing unit (GPU), permitting reduction of the load on the CPU and accelerating the simulations.

The above-described physiological parameter estimation methods make use of meshless simulation frameworks for modeling blood flow through the cardiac region. Meshless methods offer in particular the following main advantages over known ("classical") simulation frameworks.

Firstly, meshless simulations are not sensitive to the quality of image segmentation, and can directly be carried out for instance upon (e.g. automatically) segmented registered images, or a 4D model constructed from the images.

Secondly, blood flow simulations using meshless techniques can be performed faster than with mesh-based techniques. For example blood flow simulation for a full heart cycle may be run almost in real time (30-90 seconds using currently available processing hardware). By way of comparison, simulations for a full blood cycle executed for a mesh based simulation technique typically last for between 30 minutes and 2 hours, in addition also to time expended on preliminary geometry preparation, meshing, and post-processing of the results.

Thirdly, meshless simulations are stable universally across all patients, regardless of the specific geometry of their cardiac region.

As a consequence of this, while simulation results are patient-specific, the simulation workflow is patient independent.

Therefore, manual intervention of a specialist in setting up and configuring the simulation is not required.

As mentioned above, according to one or more embodiments the meshless simulation framework may be applied directly to voxels of the received series of medical images. In this case no segmentation is required. In this case, tissue geometry and positioning is estimated based simply on intensity of the image voxels. Image filtering may first be applied in this case to enhance borders.

A further aspect of the various embodiments may provide a processing unit, configured to:

receive an input time-series of three-dimensional medical images representative of a cardiac region of a patient;

apply a meshless simulation framework to simulate blood flow through at least a portion of the imaged cardiac region, wherein the simulation framework comprises simulating force interactions between elements of a simulated fluid, representing blood, and patches of a tissue structure of the cardiac region represented by the time series of images; and determine one or more physiological parameters based on the simulated blood flow.

Figure 3:
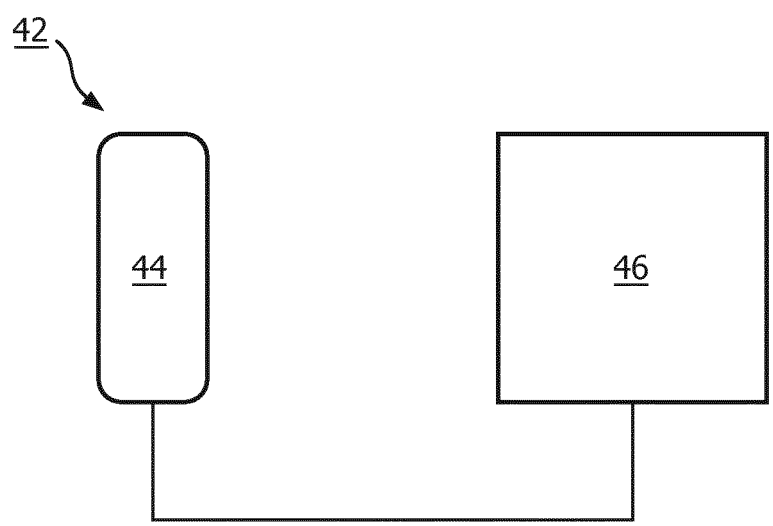
FIG. 3 schematically depicts an example medical imaging unit according to one or more embodiments of the invention.

Additionally, various embodiments may provide a medical imaging unit. An example is shown in FIG. 3. The medical imaging unit 42 comprises:

a medical imaging device 44 for acquiring a time series of three dimensional medical images; and a processing unit 46 as set out above or as set out in any claim of this application, and arranged to receive the acquired time series of three dimensional images from the medical imaging device for use in said meshless simulation framework to determine the one or more physiological parameters.

The processing unit may in particular examples receive the images in real time. For example the medical imaging device may be adapted to output the images in real time with their acquisition. The processing unit may be adapted to perform the simulation technique in real time with receipt of the medical images from the medical imaging device.

The medical imaging device may include for instance any one of: an ultrasound imaging device (such as an ultrasound transducer unit), an X-ray imaging device, an MRI imaging device, or a CT imaging device. These represent illustrative examples only.

As discussed above, embodiments of a medical imaging unit may make use of a processing unit to perform the data processing. The processing unit may be or may comprise a processor. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed embodiments, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together

The invention claimed is:

1. A method of estimating one or more physiological parameters based on medical imaging data, the method comprising:
   receiving an input time-series of three-dimensional medical images representative of a cardiac region of a patient;
   applying a meshless simulation framework to simulate blood flow through at least a portion of the imaged cardiac region, wherein the simulation framework comprises simulating force interactions between elements of a simulated fluid, representing blood, and patches of a tissue structure of the cardiac region represented by the time series of images; and
   determining one or more physiological parameters based on the simulated blood flow;
   wherein the meshless simulation framework comprises at least one of:
   i) applying an interaction potential force between the elements of the simulated fluid, and the patches of the tissue structure of the cardiac region, wherein the applied interaction potential force, F, has the form $$F = \frac{C_1}{R^a} - \frac{C_2}{R^b}$$

where C1 and C2 are pre-determined constants, R is a distance between the elements of the simulated fluid and the patches of an anatomical model of the tissue structure, and a, b are predetermined constants;
   ii) modeling an aortic pressure of the imaged cardiac region based on applying a fluid interface within the cardiac region and applying a repulsive potential force between the interface and elements of the modeled fluid; or
   iii) applying a pressure correction procedure, which comprises adding a pressure correction term to a pressure parameter assigned to each element of the fluid, the pressure correction term comprising a Taylor expansion of a Poisson equation for pressure; and
   wherein the one or more physiological parameter measurements include at least one of: a pressure change from a first point in a fluid path of the cardiac region to a second point in the fluid path, a pressure change between two points along a cardiac valve, cardiac output, a flow speed of blood through a cardiac valve, and a residence time for blood in a ventricle of the heart.

2. The method of claim 1, wherein the meshless simulation framework is a smoothed particle hydrodynamics, SPH, simulation technique.

3. The method of claim 1, wherein the simulating force interactions comprises simulating potential force interactions between individual elements of the simulated fluid and the patches of the tissue structure of the cardiac region, or wherein the simulated force interactions each comprise one or more force components, each component having an inverse power dependency upon a distance between the fluid element concerned and the tissue structure patch concerned.

4. The method of claim 1, wherein individual patches of the tissue structure are identified based on a segmentation procedure applied to the input time-series of medical images.

5. The method of claim 1, wherein the method comprises generating a 4D anatomical model of the cardiac region of the patient based on the input time-series of three-dimensional medical images, the 4D anatomical model representing the tissue structure of the cardiac region, and wherein the 4D anatomical model is used as an input for the meshless simulation framework.

6. The method of claim 1, wherein the simulation framework includes modeling an aortic pressure of the imaged cardiac region based on applying a fluid interface within the cardiac region and applying a repulsive potential force between the interface and elements of the modeled fluid.

7. The method of claim 1, wherein the pressure correction procedure is an iterative procedure, the pressure correction term being re-calculated and added to the pressure parameter at each of a series of iterations.

8. The method of claim 1, wherein the method comprises simulating blood flow through at least the aortic or mitral valve of the heart.

9. The method of 1, wherein applying the meshless simulation framework and determining the one or more physiological parameters is performed in real time with receipt of the three dimensional medical images.

10. A hardware processing unit configured to receive an input time-series of three-dimensional medical images representative of a cardiac region of a patient;
   apply a meshless simulation framework to simulate blood flow through at least a portion of the imaged cardiac region, wherein the simulation framework comprises simulating force interactions between elements of a simulated fluid, representing blood, and patches of a tissue structure of the cardiac region represented by the time series of images; and
   determine one or more physiological parameters based on the simulated blood flow;
   wherein the meshless simulation framework comprises at least one of:
   i) applying an interaction potential force between the elements of the simulated fluid, and the patches of the tissue structure of the cardiac region, wherein the applied interaction potential force, F, has the form $$F = \frac{C_1}{R^a} - \frac{C_2}{R^b}$$

where C1 and C2 are pre-determined constants, R is a distance between the elements of the simulated fluid and the patches of an anatomical model of the tissue structure, and a, b are predetermined constants;
   ii) modeling an aortic pressure of the imaged cardiac region based on applying a fluid interface within the cardiac region and applying a repulsive potential force between the interface and elements of the modeled fluid; and iii) applying a pressure correction procedure, which comprises adding a pressure correction term to a pressure parameter assigned to each element of the fluid, the pressure correction term comprising a Taylor expansion of a Poisson equation for pressure;
   and wherein the one or more physiological parameter measurements include at least one of: a pressure change from a first point in a fluid path of the cardiac region to a second point in the fluid path, a pressure change between two points along a cardiac valve, cardiac output, a flow speed of blood through a cardiac valve, and a residence time for blood in a ventricle of the heart.

11. A medical imaging unit, comprising:
a medical imaging device for acquiring a time series of three dimensional medical images; and
a processing unit as claimed in claim 10, arranged to receive the acquired time series of three dimensional images for use in said meshless simulation framework to determine the one or more physiological parameters.

12. A non-transitory computer readable medium storing instructions for estimating one or more physiological parameters based on medical imaging data that, when executed by one or more processors, cause the one or more processors to:
receive an input time-series of three-dimensional medical images representative of a cardiac region of a patient;
apply a meshless simulation framework to simulate blood flow through at least a portion of the imaged cardiac region, wherein the simulation framework comprises simulating force interactions between elements of a simulated fluid, representing blood, and patches of a tissue structure of the cardiac region represented by the time series of images; and
determine one or more physiological parameters based on the simulated blood flow;
wherein the meshless simulation framework comprises at least one of:
i) applying an interaction potential force between the elements of the simulated fluid, and the patches of the tissue structure of the cardiac region, wherein the applied interaction potential force, F, has the form $$F = \frac{C_1}{R^a} - \frac{C_2}{R^b}$$

where C1 and C2 are pre-determined constants, R is a distance between the elements of the simulated fluid and the patches of an anatomical model of the tissue structure, and a, b are predetermined constants;
ii) modeling an aortic pressure of the imaged cardiac region based on applying a fluid interface within the cardiac region and applying a repulsive potential force between the interface and elements of the modeled fluid; or
iii) applying a pressure correction procedure, which comprises adding a pressure correction term to a pressure parameter assigned to each element of the fluid, the pressure correction term comprising a Taylor expansion of a Poisson equation for pressure; and
wherein the one or more physiological parameter measurements include at least one of: a pressure change from a first point in a fluid path of the cardiac region to a second point in the fluid path, a pressure change between two points along a cardiac valve, cardiac output, a flow speed of blood through a cardiac valve, and a residence time for blood in a ventricle of the heart.

13. The non-transitory computer readable medium of claim 12, wherein the meshless simulation framework is a smoothed particle hydrodynamics, SPH, simulation technique.

14. The non-transitory computer readable medium of claim 12, wherein the simulating force interactions comprises simulating potential force interactions between individual elements of the simulated fluid and the patches of the tissue structure of the cardiac region, or wherein the simulated force interactions each comprise one or more force components, each component having an inverse power dependency upon a distance between the fluid element concerned and the tissue structure patch concerned.

15. The non-transitory computer readable medium of claim 12, wherein individual patches of the tissue structure are identified based on a segmentation procedure applied to the input time-series of medical images.

16. The non-transitory computer readable medium of claim 12, wherein the instructions further cause the one or more processors to generate a 4D anatomical model of the cardiac region of the patient based on the input time-series of three-dimensional medical images, the 4D anatomical model representing the tissue structure of the cardiac region, and wherein the 4D anatomical model is used as an input for the meshless simulation framework.

* * * * *